US006027716A

United States Patent [19]
Levin et al.

[11] Patent Number: 6,027,716
[45] Date of Patent: Feb. 22, 2000

[54] SYNERGISTIC HERBAL EXTRACTS

[75] Inventors: Orna Levin, Kfar-Neter; Doron Friedman, Karme-Yosef; Yochanan Forman, Kibbutz Maabarot; Michael Friedman, Jerusalem, all of Israel

[73] Assignee: Farmo-Nat Ltd., Ashkelon, Israel

[21] Appl. No.: 08/825,798

[22] Filed: Apr. 2, 1997

[51] Int. Cl.⁷ .............................. A61K 7/26; A61K 35/78
[52] U.S. Cl. ........................................ 424/58; 424/195.1
[58] Field of Search ............................ 424/49, 58, 195.1

[56] References Cited

U.S. PATENT DOCUMENTS

| | | | |
|---|---|---|---|
| 4,933,177 | 6/1990 | Grollier et al. | 424/63 |
| 5,525,340 | 6/1996 | Fukunaga | 424/195.1 |
| 5,626,837 | 5/1997 | Shimada et al. | 424/49 |

Primary Examiner—Peter F. Kulkosky
Attorney, Agent, or Firm—Mark M. Friedman

[57] ABSTRACT

A synergistic anti-bacterial composition, including: (a) an extract of botanical materials, the botanical materials including material from Plantago species, Hypericum species, Echinacea species and Propolis; and (b) oil of cinnamon.

12 Claims, 6 Drawing Sheets

SYNERGISTIC HERBAL EXTRACTS

FIELD AND BACKGROUND OF THE INVENTION

The present invention relates to a combination of an herbal extract and an essential oil which shows unexpected synergistic anti-microbial activity and, more particularly, to such a combination which can exert anti-microbial activity in the oral cavity and on mucosal organs.

Recently, interest has been displayed in the medicinal properties of herbal preparations. Herbal preparations are considered "more natural" and are therefore viewed as less toxic by the consumer. These preparations are being sold for a number of indications, including anti-bacterial activity.

For example, a combination of Echinacea (*Echinaceae angustifoliae radix*) and Plantago (*Plantago major*) is available from Dolisos Laboratoires, Israel, as "Plantspray". Plantspray is intended as a composition for oral hygiene. According to the product literature, Plantspray has anti-bacterial activity in the oral cavity and can therefore promote the general health of oral tissues, as well as cosmetic concerns such as malodorous breath. Another herbal combination, Echinacea and Propolis, is also available from Dolisos Laboratoires as "Echinacea Propolis Tabs". Propolis wax is the resinous substance found in beehives. The echinacea and propolis wax combination is also intended for oral hygiene.

However, although combinations of herbal extracts have enjoyed commercial success, relatively few of these combinations have demonstrated proven synergistic anti-microbial activity.

Synergistic combinations of non-herbal, anti-bacterial compositions are well known in the prior art. In certain of these combinations, one ingredient has high anti-bacterial activity alone, while the other ingredient has little or no anti-bacterial activity. In combination, however, these two ingredients have far higher anti-bacterial activity than could be expected from their individual activities, thus displaying synergism. One example of such a combination is amoxicillin and clavulanate. Alone, clavulanate has little anti-bacterial activity, but in combination with amoxicillin, it shows highly synergistic activity [*Goodman and Gilman's The Pharmacological Basis of Therapeutics*, A. G. Gilman et al., eds., Pergamon Press, Inc., 1990, p. 1093].

The advantage of such synergism is that the effectiveness of the anti-bacterial composition is greatly increased, without a concomitant increase in the dosage level or rate of administration. Lower quantities of each substance could potentially be administered in combination yet still achieve the desired therapeutic effect. Such synergistic combinations could prove particularly important in the treatment of delicate or sensitive tissues, such as the oral mucosa, where the ability to reduce the concentration of individual ingredients could prove important. Unfortunately, as noted above, although many combinations of herbal preparations are touted as having "anti-microbial activity", few have proven synergistic, rather than merely additive, activity.

There is thus a widely recognized need for, and it would be highly advantageous to have, a herbal preparation with proven synergistic anti-microbial activity, particularly for oral hygiene.

SUMMARY OF THE INVENTION

According to the present invention, there is provided a synergistic anti-microbial composition, including a herbal extract and an essential oil in a synergistic ratio. Preferably, the herbal extract is a tincture. Preferably, the composition also includes a suitable pharmaceutical carrier. Preferably, the essential oil is selected from the group consisting of cinnamon oil, cajeput oil, citronella oil, eucalyptus oil, fennel oil, geranium oil, girofle oil, lavender oil, lemon oil, spearmint oil, myrte oil, origano oil, pine oil, rosemary oil, sarriette oil, thyme oil, and tea-tree oil. Most preferably, the essential oil is selected from the group consisting of cinnamon oil, tea-tree oil and citronella oil. Preferably, the essential oil is present at a concentration of from about 0.02 to about 5 percent weight per weight, and most preferably from about 0.2 percent to about 2.0 percent weight per weight.

According to further preferred features of the present invention, the tincture includes a material selected from the group consisting of Plantago, Hypericum, Echinacea, Baptisia, Calendula, Myrrah, Phytolaca, Salvia, Catechu black, Coneflower, Krameria, Tsuga, Rosmarinus, Styrax, Crataegus, Glycerrhiza, Angelica, Krameria, Matricaria, Mallow, Propolis and Sage. Preferably, the tincture includes a mixture of Plantago, Hypericum, Echinacea and Propolis. Alternatively and preferably, the tincture includes a mixture of Plantago, Hypericum, Coneflower and Propolis. Most preferably, Plantago is present in a concentration of about 1.5 percent weight per weight, Hypericum is present in a concentration of about 1.5 percent weight per weight, Coneflower is present in a concentration of about 1.0 percent weight per weight, and Propolis is present in a concentration of about 1.0 percent weight per weight. Alternatively and preferably, the tincture is present in a concentration of from about 0.5 percent to about 20 percent weight per weight, and most preferably from about 1 percent to about 10 percent weight per weight.

According to another embodiment of the present invention, there is provided a method of treating a subject with a microbial infection, including the step of administering a synergistic anti-microbial composition to the subject, the composition including a herbal extract and an essential oil in a synergistic ratio. Preferably, the herbal extract is a tincture. Preferably, the microbial infection is selected from the group consisting of bacterium, fungus, virus and parasite.

According to yet another embodiment of the present invention, there is provided a mouthwash, including: (a) a herbal extract and an essential oil in a synergistic ratio; and (b) a pharmaceutical carrier. Preferably, the herbal extract is a tincture. Preferably, the essential oil is selected from the group consisting of citronella oil and cinnamon oil. Also preferably, the tincture includes Plantago, Hypericum, Echinacea and Propolis. Alternatively and preferably, the tincture includes Baptisia, Echinacea, Salvia, Propolis and Myrrha. Also alternatively and preferably, the tincture includes Plantago, Hypericum, Coneflower and Propolis.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
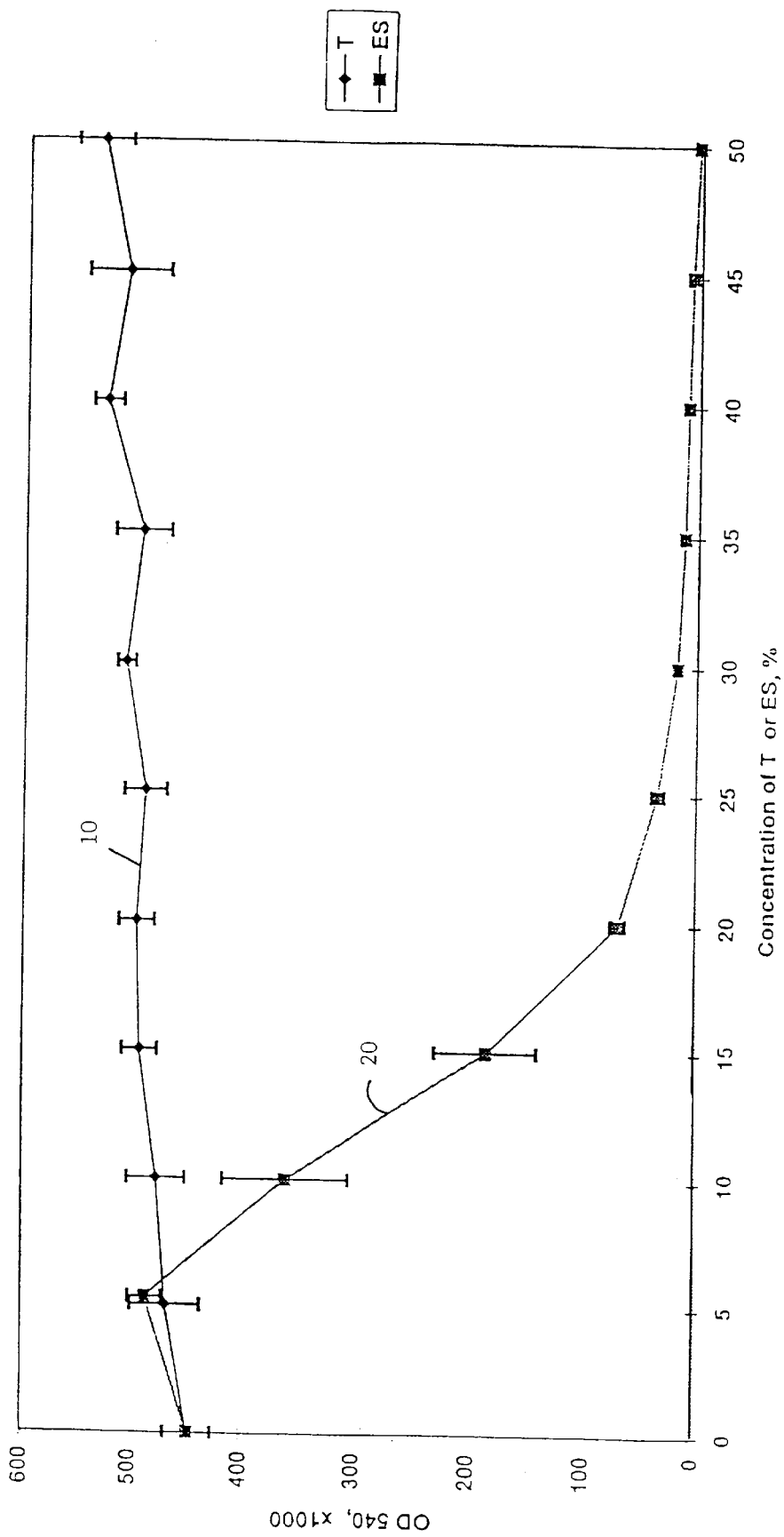
FIG. 1 is a graph illustrating the anti-microbial effect of the present invention.

The present invention is of a synergistic composition of herbal extracts which has anti-microbial activity. Specifically, the present invention can be used to combat microbial infection in a variety of environments, including the oral cavity. Hereinafter, the term "microbe" will refer to bacteria and fungi, as well as viruses and parasites.

This synergistic anti-microbial composition includes two components. The first component, an essential oil, has anti-microbial activity. The second component, which includes a herbal extract of botanical materials, such as a tincture, has significantly lower activity, or no anti-microbial activity, alone. However, the second component significantly potentiates the anti-microbial activity of the first component, indicating the presence of synergism between the two components.

The first component can be any one of a number of different essential oils. An essential oil is a volatile mixture of esters, aldehydes, alcohols, ketones and terpenes, which can be prepared from botanical materials or plant cell biomass from cell culture. Examples of essential oils include, but are not limited to, oil of cinnamon, prepared from the dried bark of the roots of *Cinnamomum zeyloriaceae;* cajeput oil, eucalyptus oil, prepared from the fresh leaves and branches of various species of Eucalyptus, such as *E. globulus;* fennel oil, prepared from dried ripe fruit of *Foeniculum vulgare;* geranium oil, prepared from the aerial parts of Pelargonium species; girofle oil, lavander oil, prepared from fresh flowering tops of Lavandula species such as *Lavandula officinalis;* lemon oil, obtained from the fresh peel of *Citrus limon;* spearmint oil, prepared form the overground parts of fresh flowering Mentha species, such as *M. spicata;* myrte oil, origano oil, pine oil, rosemary oil, prepared from tops or leafy twigs of *Rosmarinus officinalis;* sarriette oil, thyme oil, prepared from the leaves and flowering tops of *Thymus vulgaris;* and tea-tree oil, obtained from the leaves of *Melaleuca olternifolia.*

Essential oils can be prepared by subjecting botanical materials to a distillation process, for example. A number of different procedures can be used for distillation. One such example, using dried bark of the shoots of *Cinnamomum zeyloriaceae,* is given for illustrative purposes only and is not intended to be limiting. First, the bark is placed in a suitable still with sufficient purified water. Next, the bark is distilled with steam from the water. The steam is then condensed and the oil phase is separated from the aqueous phase to obtain the essential oil. All of the above essential oils are also available commercially. In the preparations of the present invention, the essential oils, such as cinnamon oil, contain not less than about 1.2% weight per volume of volatile oil.

The second component is a herbal extract, such as a tincture of botanical materials, which prepared by contacting botanical material with a solvent [*British Herbal Pharmacopoeia,* Peter R. Bradley, ed., British Herbal Medicine Association, 1983; and *British Herbal Compendium,* Peter R. Bradley, ed., British Herbal Medicine Association, 1992]. The solvent can be aqueous or organic, or a combination thereof. Acceptable organic solvents include, but are not limited to, glycerin, propylene glycol or alcohol, or a combination thereof. The most preferred solvents are hydroalcoholic solvents as defined in *British Herbal Pharmacopoeia and Compendium.* The botanical material can include, but is not limited to, one or more of the following species: Plantago (*Plantago major*), Hypericum (*Hypericaceae perforatus*), Echinacea (Echinaceae species such as *Echinaceae angustifoliae radix* and *Echinaceae purpurea*), Baptisia, Calendula, Myrrah, Phytolaca, Salvia, Catechu black, Krameria, Tsuga, Rosmarinus, Styrax, Crataegus, Glycerrhiza (*Glycerrhiza glabra*), Angelica, Krameria, Matricaria, Mallow and Sage. The most preferred tincture of botanical materials is prepared by combining extracts of Plantago (*Plantago major*), Hypericum (*Hypericaceae perforatus*), Echinacea (*Echinaceae angustifoliae radix*) and Propolis, which is the resinous substance found in beehives. Although strictly speaking Propolis is not a botanical material, extracts of this material are prepared in a substantially similar manner as extracts of the plant materials. These extracts can be prepared according to one of the following methods, although of course other methods could be used, and are also available commercially.

In the first method, the botanical materials are macerated with a solvent. The solvent is allowed to remain in contact with the botanical materials for an appropriate period of time and is then filtered to remove solid or particulate material in order to form a filtered extract. If desired, additional solvent can be added to the filtered extract to bring it to a final volume. Alternatively, solvent can be evaporated to increase the concentration of the active constituents of the extract.

In the second method, the botanical materials are percolated with a solvent. The botanical materials are placed in a column, known as a percolator. The solvent is then allowed to flow through the column, contacting the botanical methods, and is collected. The collected solvent forms the extract. Percolation has the advantage of allowing a minimal volume of solvent to be used during the extraction process. The volume of solvent required can be partially controlled by the rate of fluid flow through the column, allowing for greater control over the final volume of extract. Preferably, the flow of solvent out of the column is stopped entirely during extraction, so that the efficiency of extraction is increased. This represents a combination of maceration and percolation.

If either method, or a combination of both methods, is used to prepare extracts of the above botanical materials, preferably alcoholic or hydroalcoholic solvents are used. Most preferably, the botanical materials are harvested no more than 24 hours previously, so that these materials are fresh.

In the present invention, these extracts of the botanical materials were used directly as tinctures. Hereinafter, the term "tincture" refers to an extract of either the botanical materials or of Propolis, prepared substantially as described above.

The anti-microbial activity of certain tinctures and essential oils was tested separately and in combination, according to the following protocol. The first combination used cinnamon oil and the first tincture. The first tincture included extracts of Plantago, Hypericum, Echinacea and Propolis. The second combination used citronella oil and the second tincture. The second tincture included extracts of Baptisia, Echinacea, Salvia, Propolis and Myrrha. The anti-microbial activity of the two components of each combination, the essential oil and the tincture, was tested by the laboratory of Dr. Doron Steinberg in the Hebrew University School of Dentistry, Jerusalem, Israel. The laboratory was not informed of the identity of each component. Substantially similar testing protocols were followed for each combination.

EXAMPLE 1

Testing of the First Composition and General Test Protocol

In this Example, the testing protocol, which was used for both compositions of the present invention, is described, and results are given for the first composition. The first composition included cinnamon oil and the first tincture.

The synergistic anti-microbial activity of the two components was checked by using plaque bacterium of the type *Streptococcus sobrinus* 6715, which infects the oral cavity in humans. The concentration of each of the components were varied from about 0 to about 50%. Different ratios of these components were tested. The various concentrations and ratios tested are given in Table 1. In all, 60 different combinations were tested, each combination representing a different test composition.

TABLE 1

Protocol
(*St. sobrinus* 6715, after 24 h incubation)

T →

| ES % | 0 | 5 | 10 | 15 | 20 | 25 | 30 | 35 | 40 | 45 | 50 |
|---|---|---|---|---|---|---|---|---|---|---|---|
| 0 | 0 | 100 | 200 | 300 | 400 | 500 | 600 | 700 | 800 | 900 | 1000 |
|   | 0 | 0 | 0 | 0 | 0 | 0 | 0 | 0 | 0 | 0 | 0 |
|   | 1000 | 900 | 800 | 700 | 600 | 500 | 400 | 300 | 200 | 100 | 0 |
|   | 800 | 800 | 800 | 800 | 800 | 800 | 800 | 800 | 800 | 800 | 800 |
|   | 190 | 190 | 190 | 190 | 190 | 190 | 190 | 190 | 190 | 190 | 190 |
| 5 | 0 | 100 | 200 | 300 | 400 | 500 | 600 | 700 | 800 | 900 |   |
|   | 100 | 100 | 100 | 100 | 100 | 100 | 100 | 100 | 100 | 100 |   |
|   | 900 | 800 | 700 | 600 | 500 | 400 | 300 | 200 | 100 | 0 |   |
|   | 800 | 800 | 800 | 800 | 800 | 800 | 800 | 800 | 800 | 800 |   |
|   | 190 | 190 | 190 | 190 | 190 | 190 | 190 | 190 | 190 | 190 |   |
| 10 | 0 | 100 | 200 | 300 | 400 | 500 | 600 | 700 | 800 |   |   |
|   | 200 | 200 | 200 | 200 | 200 | 200 | 200 | 200 | 200 |   |   |
|   | 800 | 700 | 600 | 500 | 400 | 300 | 200 | 100 | 0 |   |   |
|   | 800 | 800 | 800 | 800 | 800 | 800 | 800 | 800 | 800 |   |   |
|   | 190 | 190 | 190 | 190 | 190 | 190 | 190 | 190 | 190 |   |   |
| 15 | 0 | 100 | 200 | 300 | 400 | 500 | 600 | 700 |   |   |   |
|   | 300 | 300 | 300 | 300 | 300 | 300 | 300 | 300 |   |   |   |
|   | 700 | 600 | 500 | 400 | 300 | 200 | 100 | 0 |   |   |   |
|   | 800 | 800 | 800 | 800 | 800 | 800 | 800 | 800 |   |   |   |
|   | 190 | 190 | 190 | 190 | 190 | 190 | 190 | 190 |   |   |   |
| 20 | 0 | 100 | 200 | 300 | 400 | 500 | 600 |   |   |   |   |
|   | 400 | 400 | 400 | 400 | 400 | 400 | 400 |   |   |   |   |
|   | 600 | 500 | 400 | 300 | 200 | 100 | 0 |   |   |   |   |
|   | 800 | 800 | 800 | 800 | 800 | 800 | 800 |   |   |   |   |
|   | 190 | 190 | 190 | 190 | 190 | 190 | 190 |   |   |   |   |
| 25 | 0 | 100 | 200 | 300 | 400 | 500 |   |   |   |   |   |
|   | 500 | 500 | 500 | 500 | 500 | 500 |   |   |   |   |   |
|   | 500 | 400 | 300 | 200 | 100 | 0 |   |   |   |   |   |
|   | 800 | 800 | 800 | 800 | 800 | 800 |   |   |   |   |   |
|   | 190 | 190 | 190 | 190 | 190 | 190 |   |   |   |   |   |
| 30 | 0 | 100 | 200 | 300 | 400 |   |   |   |   |   |   |
|   | 600 | 600 | 600 | 600 | 600 |   |   |   |   |   |   |
|   | 400 | 300 | 200 | 100 | 0 |   |   |   |   |   |   |
|   | 800 | 800 | 800 | 800 | 800 |   |   |   |   |   |   |
|   | 190 | 190 | 190 | 190 | 190 |   |   |   |   |   |   |
| 35 | 0 | 100 | 200 | 300 |   |   |   |   |   |   |   |
|   | 700 | 700 | 700 | 700 |   |   |   |   |   |   |   |
|   | 300 | 200 | 100 | 0 |   |   |   |   |   |   |   |
|   | 800 | 800 | 800 | 800 |   |   |   |   |   |   |   |
|   | 190 | 190 | 190 | 190 |   |   |   |   |   |   |   |
| 40 | 0 | 100 | 200 |   |   |   |   |   |   |   |   |
|   | 800 | 800 | 800 |   |   |   |   |   |   |   |   |
|   | 200 | 100 | 0 |   |   |   |   |   |   |   |   |
|   | 800 | 800 | 800 |   |   |   |   |   |   |   |   |
|   | 190 | 190 | 190 |   |   |   |   |   |   |   |   |
| 45 | 0 | 100 |   |   |   |   |   |   |   |   |   |
|   | 900 | 900 |   |   |   |   |   |   |   |   |   |
|   | 100 | 0 |   |   |   |   |   |   |   |   |   |
|   | 800 | 800 |   |   |   |   |   |   |   |   |   |
|   | 190 | 190 |   |   |   |   |   |   |   |   |   |
| 50 | 0 |   |   |   |   |   |   |   |   |   |   |
|   | 1000 |   |   |   |   |   |   |   |   |   |   |

TABLE 1-continued

Protocol
(*St. sobrinus* 6715, after 24 h incubation)

| T → | | | | | | | | | | | |
|---|---|---|---|---|---|---|---|---|---|---|---|
| ES % | 0 | 5 | 10 | 15 | 20 | 25 | 30 | 35 | 40 | 45 | 50 |
| ↓ | 0 | | | | | | | | | | |
| | 800 | | | | | | | | | | |
| | 190 | | | | | | | | | | |

T, mkl
ES, mkl
Blanc, mkl
Medium mkl
Bacteries, mkl

Each combination has five ingredients. The volume of each ingredient is given in microliters. The ingredients are given in the same order in each box, which represents one combination. The ingredients are as follows: tincture, essential oil, vehicle, medium and bacteria.

Cinnamon oil was contained in the following preparation (all percentages are weight/weight): 10% glycerol, 2.5% ethanol, 1.8% Tween 20, 0.03% sodium saccharin and 0.2% cinnamon oil, with water as the remaining ingredient. The cinnamon oil is the active ingredient; the other ingredients are often used in mouthwashes to form a suitable carrier.

The first tincture was contained in the following preparation (all percentages are weight/weight): 10% glycerol, 2.5% ethanol, 1.8% Montanox 80, 0.03% sodium saccharin, 1.5% Plantago extract, 1.5% Hypericum extract, 1.0% Echinacea extract and 1.0% Propolis extract, with water as the remaining ingredient. The tincture, consisting of the extracts of Plantago, Hypericum, Echinacea and Propolis, is the active ingredient; again, the other ingredients are a suitable carrier, and are present in the same concentrations as for the essential oil preparation.

The anti-microbial activity of the test compositions was checked as follows: the bacteria, from a frozen reservoir, were thawed at room temperature. From these bacteria, a starter was prepared (0.5 cc bacteria into 5 cc growth substrate BHI) for overnight incubation at 37° C., 5% carbon dioxide atmosphere. BHI is brain heart infusion, a nutritive broth including an infusion of calf brains and beef heart, which was purchased from Difco (Detroit, Mich., U.S.A.). BHI is a particularly favorable medium for the culture of streptococci bacteria. Normally, BHI is prepared by dissolving about 37 g of BHI powder into about 1 liter of distilled or deionized water. 3× concentrated BHI, as its name suggests, is prepared by dissolving about 111 g of BHI powder into about 1 liter of distilled or deionized water.

The tincture and the essential oil were placed into 3× concentrated BHI, in the ratios listed in Table 1, for a final volume of 1cc. To this mixture was added 1 cc of the previously prepared starter, containing the bacteria. The influence of the above-referenced materials on the bacteria were checked after the bacteria were grown overnight at 37° C., 5% $CO_2$. The anti-microbial activity of the analyzed materials was measured through the ability of the bacteria to multiply in the presence of the test compositions. The growth of the bacteria was checked in a spectrophotometer using a wavelength of 540 nm ($OD_{540}$).

As a control, each of the test compositions was checked in the spectrophotometer at 540 nm after an overnight incubation without bacteria. As a further control, each test composition with bacteria was checked in the spectrophotometer immediately, before bacterial growth and multiplication could occur, in order to examine the transmissivity of the initial bacterial preparation. The measured values from these controls were then subtracted from the results given below.

As stated above, 60 different combinations of materials were checked. Each experiment was made in triplicate. For each combination there was a control without bacteria and control without incubation. The final result is the net inhibition of the tested combination on the growth of bacteria. The results are shown as mean and standard deviation.

The principles and operation of a synergistic antimicrobial composition according to the present invention may be better understood with reference to the drawings and table, and the accompanying description. These drawings and the table give the results obtained from the above protocol.

Referring now to the drawings, FIG. 1 is a graph illustrating the anti-bacterial effect of the first composition according to the present invention, which included the first tincture and cinnamon oil as the essential oil. The effect of the first tincture (T) and of the oil of cinnamon (ES) are shown separately. A curve 10 depicting the effect of the first tincture on bacterial growth clearly demonstrates that the first tincture did not inhibit bacterial growth. However, a curve 20 showing the effect of the oil of cinnamon shows that the oil of cinnamon clearly had an anti-bacterial effect. Thus, the oil of cinnamon alone had anti-bacterial activity, which increased as the concentration of the oil was increased. A maximum effect is seen with a concentration of about 30% of oil of cinnamon. The concentration at which 50% of the bacteria were killed ($IC_{50}$) was about 10.9% of oil of cinnamon (calculated by interpolation).

Compared to the anti-bacterial activity of the oil, the first tincture alone was not found to have any anti-bacterial activity between the concentrations of about 5% and about 50%. On the contrary, from FIG. 1 the first tincture appears to positively encourage bacterial growth. It should be noted that this increase in bacterial growth is moderate. At the highest concentration of first tincture, about 50%, the first tincture caused an increase of only about 18% in the growth of the bacteria relative to the controls. Since the first tincture appeared to favor bacterial growth, the analysis of the potential synergism was adapted to the $IC_{50}$, or concentration at which 50% of the bacteria were killed, rather than to the concentration at which substantially all of the bacteria were killed, as is usually the case.

The calculation of the additive, synergistic, or antagonistic activity of the combination of the oil of cinnamon and the first tincture was done according to the following formula:

FIC (index)<1 indicates synergism

FIC (index)>1 indicates antagonism

FIC (index)=1 indicates additive effect where FIC (index) is the sum of the FIC of both the first tincture and the oil of cinnamon. The FIC, or Fractional Inhibitory Concentration, is calculated according to the following formula:

$$FIC = MIC \text{ in combination} / MIC \text{ alone}$$

where MIC is the minimal inhibitory concentration, which is the lowest concentration of a substance which measurably inhibits growth of the bacteria. Thus, "MIC in combination" is the lowest concentration of one of the ingredients, such as the oil of cinnamon, which measurably inhibits growth in the presence of the other ingredient, such as the first tincture. The "MIC alone" is the sum of the minimal inhibitory concentrations for each ingredient alone.

As stated above, the $IC_{50}$ was used, or the concentration at which 50% of bacterial growth is inhibited, instead of the classical MIC of 90 to 100% growth inhibition. The $IC_{50}$ value was determined by interpolation between the results obtained for the oil of cinnamon and extrapolation between the results obtained for the first tincture. Thus, the $IC_{50}$ of the first tincture was calculated as a negative value, since the first tincture positively encouraged bacterial growth.

Table 2 shows the FIC (index) obtained for varying ratios of the oil of cinnamon and the first tincture. Interestingly, the greatest synergism between these two ingredients was obtained when a relatively large amount of the first tincture, or 83% of the total composition, and a relatively small amount of the oil of cinnamon, or 17%, was used, as in composition number 9.

TABLE 2

Relation between FIC (index) and ratio of ingredients

| Test Composition | Oil of cinnamon (% of total) | First Tincture (% of total) | FIC (index) |
|---|---|---|---|
| 1 | 100 | 0 | 1.00 |
| 2 | 66 | 34 | 0.87 |
| 3 | 49 | 51 | 0.83 |
| 4 | 39 | 61 | 0.79 |
| 5 | 31 | 69 | 0.71 |
| 6 | 27 | 73 | 0.71 |
| 7 | 23 | 77 | 0.66 |
| 8 | 19 | 81 | 0.57 |
| 9 | 17 | 83 | 0.54 |

As appear from Table 2 there is synergistic activity between the two substances. While the first tincture slightly encourages the growth of the bacteria, the oil of cinnamon works as an anti-bacterial substance. In certain combinations, especially when lower concentrations of the oil of cinnamon are used, the combined effect of the two substances is a decrease in the survival of the bacteria. This is interesting because despite the supposed promotion of bacterial growth by the first tincture, the combined effect of the oil of cinnamon is bigger than the anti-bacterial effect of the cinnamon oil alone.

Figure 2:
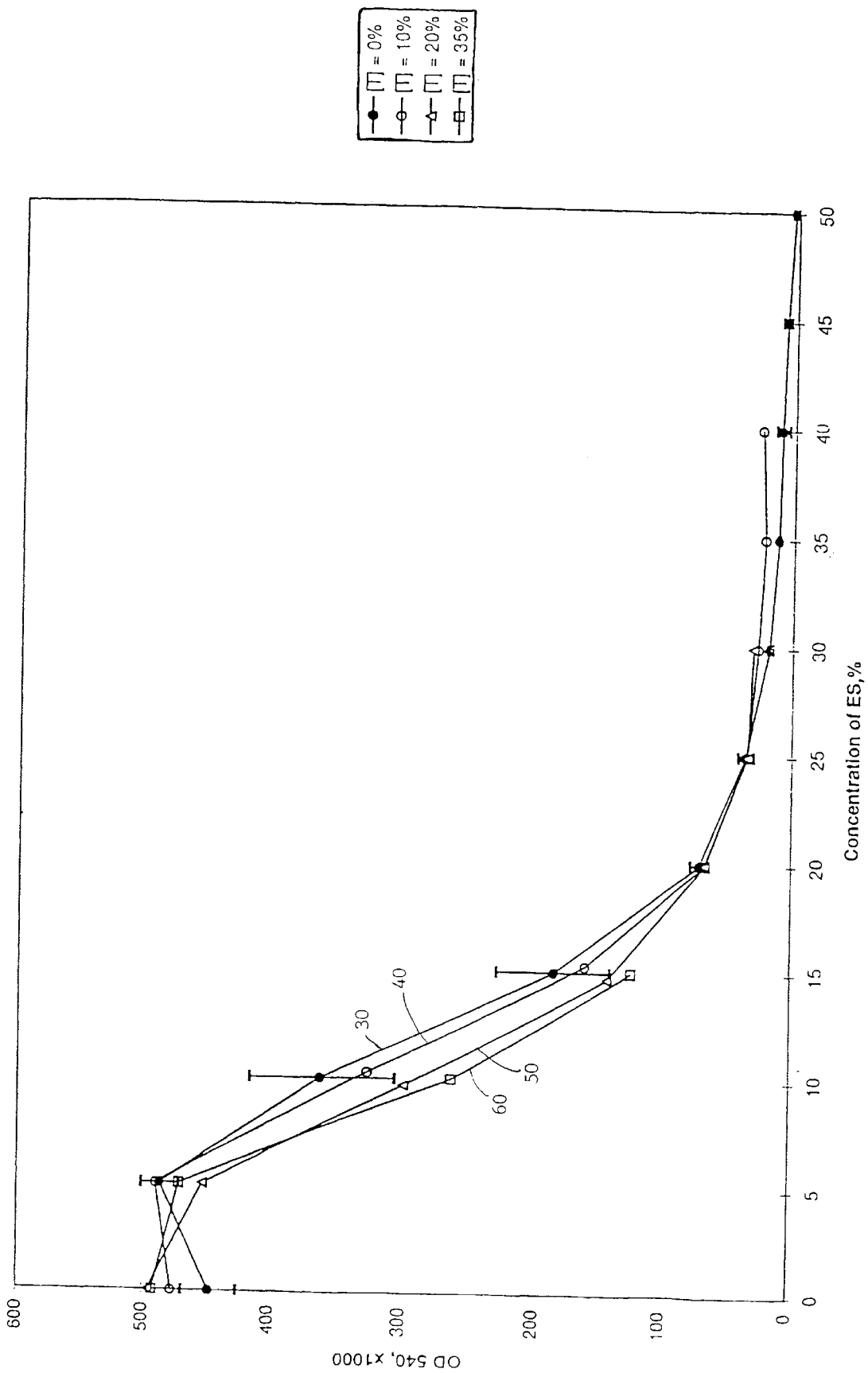
FIG. 2 is a graph illustrating the synergistic effect of different concentrations of a tincture of botanical materials within the present invention.
Figure 3:
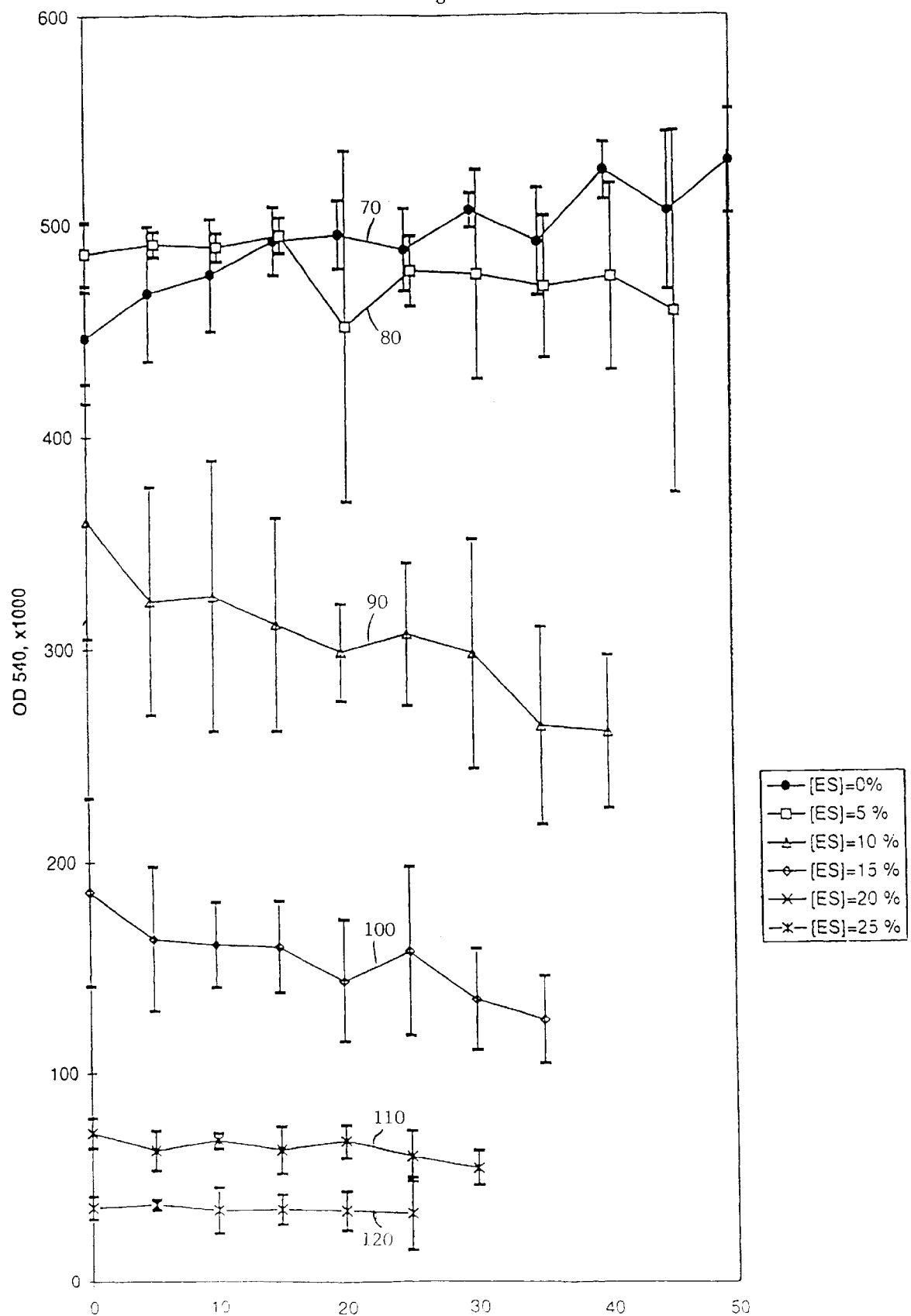
FIG. 3 is a graph illustrating the synergistic effect of different concentrations of an essential oil within the present invention.

FIGS. 2 and 3 are graphs illustrating the synergistic effect of the first oil of cinnamon. In FIG. 2, the anti-bacterial effect of a combination of increasing concentrations of oil of cinnamon and 0, 10, 20 or 35% concentration of the tincture is shown. In FIG. 3, the relation is reversed, and the anti-bacterial effect of a combination of increasing concentration of the tincture and 0, 5, 10, 15, 20 or 25% concentration of the oil of cinnamon is shown.

In FIG. 2, curve 30 shows the effect of increasing concentrations of the oil of cinnamon alone. Curve 40 shows the effect of adding 10% of the first tincture on bacterial growth. A very slight decrease in transmissivity at 540 nm, and hence of bacterial growth, is seen when between 5 and 15% of the oil of cinnamon is used. This effect is heightened by the addition of 20% or 35% of the first tincture to between 5 and 15% of the cinnamon oil, as shown in curves 50 and 60, respectively. At higher concentrations of the cinnamon oil, this apparent decrease is not seen, presumably because of the strong inhibitory effect of the cinnamon oil alone.

In FIG. 3, curve 70 shows that the first tincture alone did not inhibit bacterial growth and could have slightly encouraged such growth. Curve 80 shows that an addition of 5% of the cinnamon oil did not have a strongly inhibitory effect on bacterial growth, if indeed any inhibitory effect was shown. However, curve 90 shows that a combination of increasing concentrations of the first tincture and 10% of the oil of cinnamon demonstrates the strongest synergistic anti-bacterial activity. A somewhat weaker synergistic effect is seen in curve 100, with 15% of oil of cinnamon added. Little or no synergistic effect is seen in curves 110 or 120, with 20 or 25% of the oil of cinnamon added.

Thus, from these results, clearly oil of cinnamon and the first tincture showed a synergistic anti-bacterial effect in combination at relatively low concentrations of oil of cinnamon, such as 10 or 15%. This means that greater anti-bacterial activity can be obtained at lower concentrations of oil of cinnamon in the presence of the first tincture, which is very important in the formulation of these compositions for medicinal use.

EXAMPLE 2

Test Results for the Second Composition

The second composition, which included the second tincture and citronella oil, was tested according to a substantially similar protocol as that described above for the first composition.

The second composition included citronella oil in the same formulation as the cinnamon oil in Example 1. Specifically, citronella oil was contained in the following preparation (all percentages are weight/weight): 10% glycerol, 2.5% ethanol, 1.8% Tween 20, 0.03% sodium saccharin and 0.1% citronella oil, with water as the remaining ingredient. The citronella oil is the active ingredient; the other ingredients are often used in mouthwashes to form a suitable carrier.

The second tincture was contained in the following preparation (all percentages are weight/weight): 10% glycerol, 2.5% ethanol, 1.8% Tween 20, 0.03% sodium saccharin, 1.5% Baptisia extract, 1.5% Salvia extract, 1.0% Echinacea extract, 1.0% Myrrha extract and 1.0% Propolis extract, with water as the remaining ingredient. The tincture, consisting of the extracts of Baptisia, Salvia, Echinacea, Myrrha and Propolis, is the active ingredient; again, the other ingredients are a suitable carrier, and are present in the same concentrations as for the essential oil preparation.

As for the first composition, as described in Example 1 above, the synergistic anti-bacterial activity of the two components was checked by using plaque bacterium of the type *Streptococcus sobrinus* 6715, which infects the oral cavity in humans. The concentration of each of the components were varied from about 0 to about 50%. Different ratios of these components were tested. The various concentrations and ratios tested are as for the first composition, and are given in Table 1. In all, 60 different combinations were tested, each combination representing a different test composition. Testing protocols were substantially similar to those given in Example 1, and the results were calculated in a substantially similar manner.

The combination of citronella oil and the second tincture has a synergistic effect. Table 3 shows the FIC(index) obtained for varying ratios of the citronella oil and the second tincture, which are equivalent to those compositions in Example 1 which are designated with die numbers 1–8. Composition number 9 is missing. The FIC(index) was calculated as described in Example 1, above.

TABLE 3

Relation between FIC (index) and ratio of ingredients

| Test Composition | Citronella Oil (% of total) | Second Tincture (% of total) | FIC (index) |
| --- | --- | --- | --- |
| 1 | 100 | 0 | 1.00 |
| 2 | 66 | 34 | 0.99 |
| 3 | 49 | 51 | 0.91 |
| 4 | 39 | 61 | 0.92 |
| 5 | 31 | 69 | 0.89 |
| 6 | 27 | 73 | 0.88 |
| 7 | 23 | 77 | 0.87 |
| 8 | 19 | 81 | 0.78 |

These results show that a synergistic effect is obtained when less than 49% of the citronella oil is used. The effect is more pronounced as the composition contains more of the second tincture, and less of the citronella oil.

Figure 4:
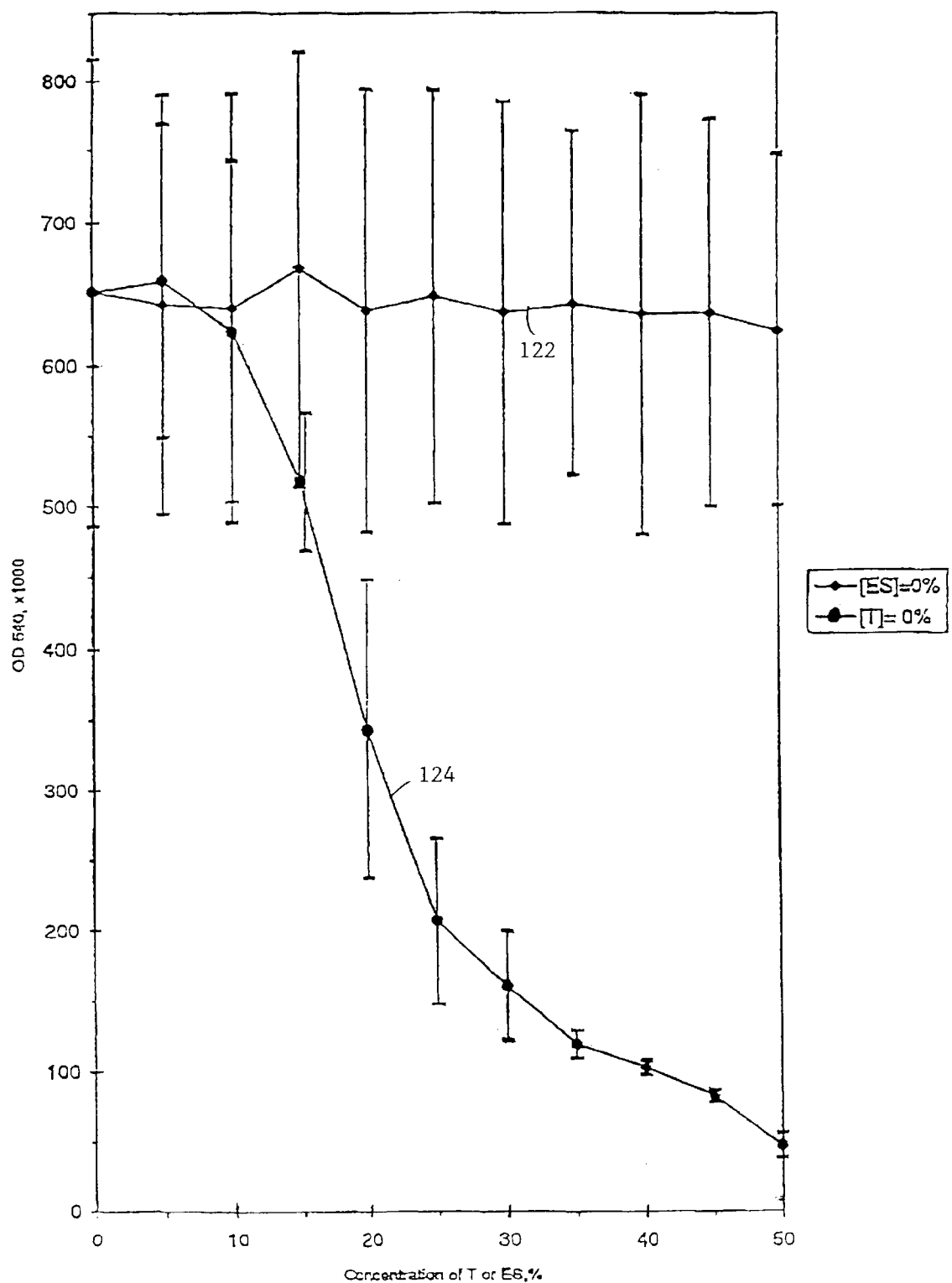
FIG. 4 is a graph illustrating the anti-microbial effect of individual components of a second embodiment of the present invention.

FIG. 4 is a graph illustrating the anti-bacterial effect of individual components of a second embodiment of the present invention. The top curve, curve 122, illustrates the lack of anti-bacterial effect of substance "T", the second tincture. The bottom curve, curve 124, illustrates the potent anti-bacterial effect of substance "ES", the essential oil, in this Example citronella oil. The maximum anti-bacterial effect of citronella oil is seen at the maximum concentration of 50%. Thus, similarly to the first tincture and essential oil tested, the second tincture has no anti-bacterial effect while the second essential oil does have such an effect.

Figure 5:
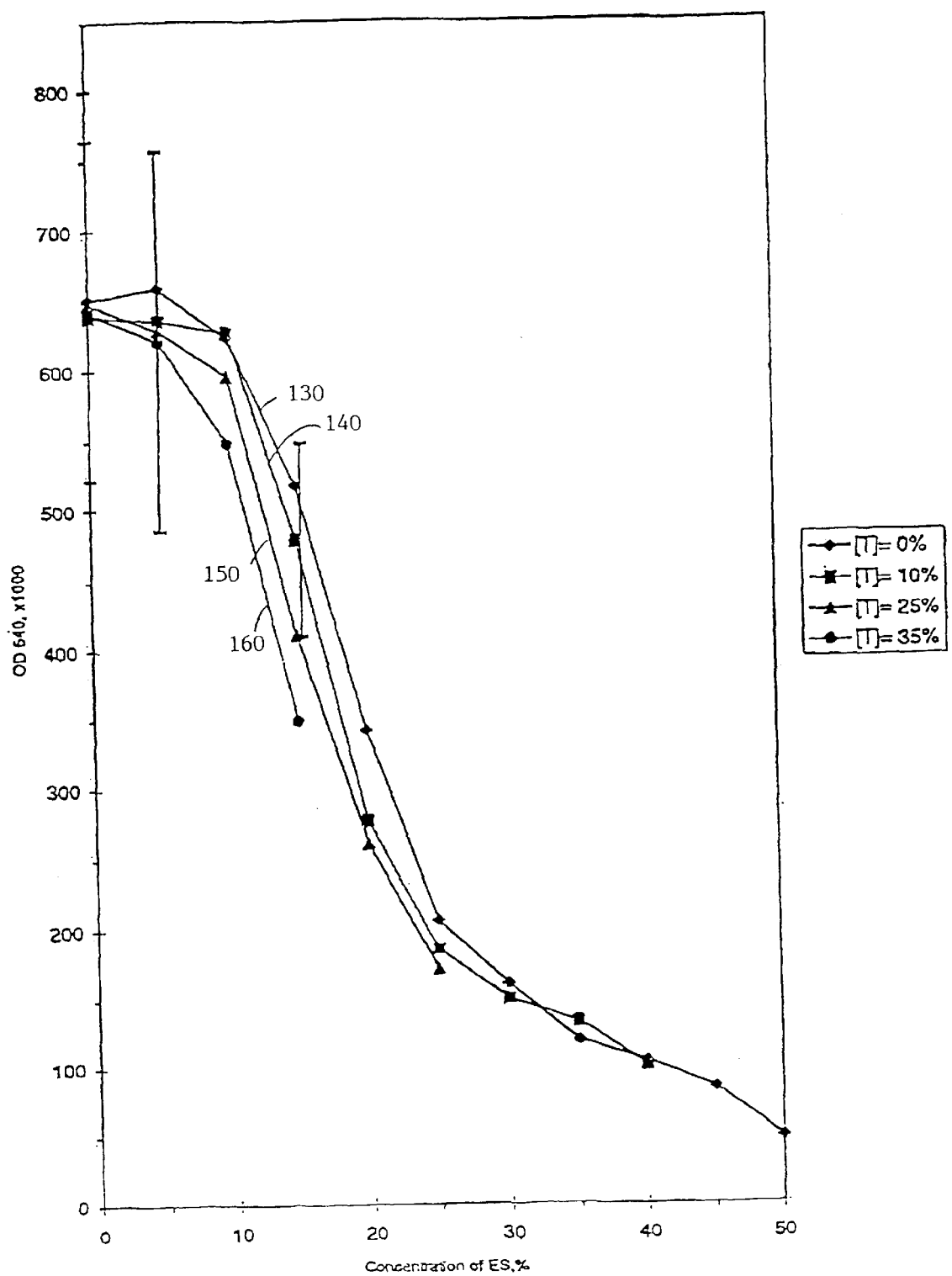
FIG. 5 is a graph illustrating the synergistic effect of different concentrations of a second tincture of botanical materials within the present invention.
Figure 6:
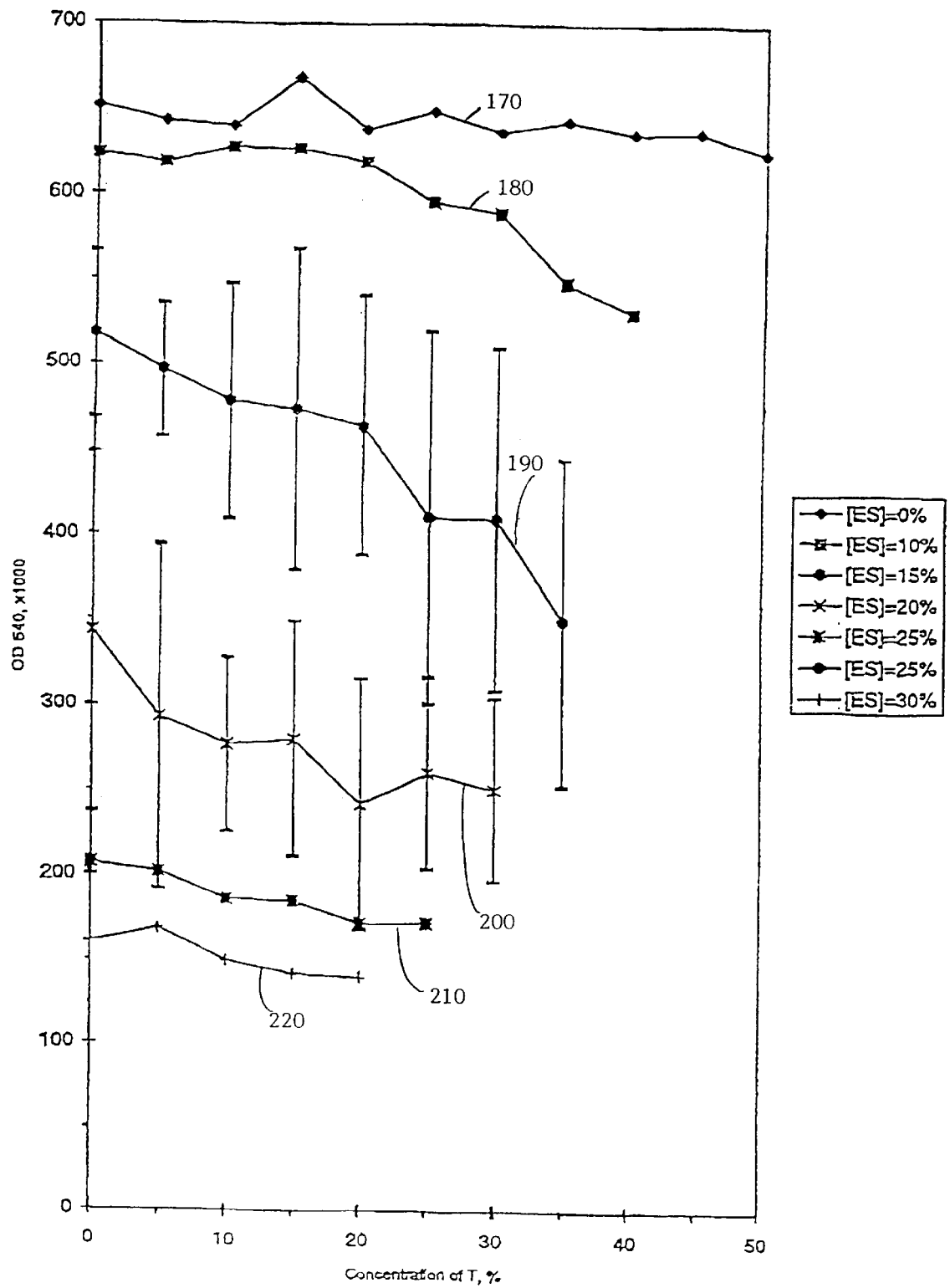
FIG. 6 is a graph illustrating the synergistic effect of different concentrations of a second essential oil within the present invention.

FIG. 5 is a graph illustrating the synergistic effect of different concentrations of the second tincture, while FIG. 6 is a graph illustrating the synergistic effect of different concentrations of the second essential oil. In FIG. 5, the anti-bacterial effect of a combination of increasing concentrations of citronella oil and 0, 10, 25 or 35% concentration of the second tincture is shown. In FIG. 6, the relation is reversed, and the anti-bacterial effect of a combination of increasing concentrations of the second tincture and 0, 10, 15, 20, 25 or 30% concentration of the citronella oil is shown.

In FIG. 5, curve 130 shows the effect of increasing concentrations of the citronella oil alone. Curve 140 shows the effect of adding 10% of the second tincture on bacterial growth. A very slight decrease in transmissivity at 540 nm, and hence of bacterial growth, is seen when between 20 and 30% of the citronella oil is used. The addition of 25% or 35% of the second tincture also results in heightened effectiveness of the citronella oil at an even lower concentration of 10%, as shown in curves 150 and 160, respectively. Thus, clearly the second tincture can increase the effectiveness of the citronella oil.

In FIG. 6, curve 170 shows that the second tincture alone did not strongly inhibit bacterial growth, if indeed any inhibitory effect was shown. Curve 180 shows that an addition of 10% of the citronella oil had an inhibitory effect on bacterial growth at concentrations of the second tincture above 20%. In fact, curve 180 demonstrates the strongest effect of the combination of the citronella oil and the second tincture. The effect of increasing concentrations of the second tincture and of the citronella oil are more difficult to assess in the remaining curves 190, 200, 210 and 220.

Thus, from these results, clearly citronella oil and the second tincture showed a synergistic anti-bacterial effect in combination at relatively low concentrations of citronella oil, such as from about 5% to about 15%, and relatively higher concentrations of the second tincture, such as from about 25% to about 35%.

EXAMPLE 3

Anti-Fungal Effects of Compositions of the Present Invention

A composition of the present invention was tested for its effect against fungal activity. The composition included 4.6% Phytolacca extract, 4.6% Coneflower extract, 3.1% Symphytum extract, 3.1% Calendula extract, 3.1% Hamamelis extract, 1.5% Propolis extract, 0.5% Thyme oil and 0.5% Lavandula oil as the active ingredients. The anti-fungal activity was tested in a similar manner as for bacteria, as described above. Specifically, two different fungal species were tested, *Candida albicans* and *Aspergillus niger.* These fungi were grown in a suitable solid growth medium, TSA (Difco, Detroit, Mich., U.S.A.) to which 10%, 5%, 2.5%, 1.25% of either the composition or alcohol (as a control) was added. As a further control, fungi were also grown without the addition of either the alcohol alone or the composition. The experiments were performed by the AminoLab Company, Rehovot, Israel, in a double-blind test. Results are shown in Table 4 below.

TABLE 4

Inhibitory Effect of the First and Second Anti-fungal Compositions

| | | Concentration of Anti-fungal Composition | | | | |
| --- | --- | --- | --- | --- | --- | --- |
| Substance | Fungus | Control | 1.25% | 2.5% | 5% | 10% |
| alcohol | *Candida* | + | + | + | + | – |
| | *Aspergillus* | 3.7 mm | 3.1 mm | 2.6 mm | 2.0 mm | 0.5 mm |
| composition | *Candida* | + | + | + | – | – |
| | *Aspergillus* | 3.7 mm | 3.8 mm | 2.5 mm | 0.5 mm | – |

As shown in Table 4, alcohol alone did slightly inhibit the growth of *Candida albicans,* with a MIC of 10%. As noted above, MIC is the minimal inhibitory concentration, which is the lowest concentration of a substance which measurably inhibits growth of the micro-organism. Alcohol alone also reduced, but did not completely inhibit, the growth of *Aspergillus niger.*

The test composition strongly inhibited the growth of *Candida albicans,* with a MIC of 5%. In addition, the test composition strongly inhibited the growth of *Aspergillus niger.* Thus, this compositions shows clear anti-fungal properties, due to the combination of the essential oil and the tincture.

Although this composition is described as an "anti-fungal composition" for the sake of clarity, it is understood that such a designation is not intended as a limitation and that this composition has many other uses as a treatment for various diseases and conditions, as further described in Example 5 below.

EXAMPLE 4

Synergistic Anti-bacterial and Anti-fungal Preparations and Methods of Administration As noted above, combinations of a tincture and an essential oil show synergistic anti-bacterial activity, as well as anti-fungal activity. These combinations can be used in a number of formulations. Furthermore, these formulations can be administered to a subject in a number of ways, which are well known in the art. For example, administration may be done topically (including ophtalmically, vaginally, rectally, intranasally), orally or by inhalation. Hereinafter, the term "subject" includes the human or mammal, including but not limited to livestock animals and pets, to whom the composition is administered.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Dosing is dependent on the severity of the symptoms and on the responsiveness of the patient to the composition. Persons of ordinary skill in the art can easily determine optimum dosages, dosing methodologies and repetition rates.

EXAMPLE 5

Methods of Treatment with the Compositions of the Present Invention

The compositions of the present invention, which include a synergistically effective amount of an essential oil and of a tincture, as described above, can be used to treat a number of different diseases and conditions. For example, these compositions can be used in a mouthwash, for oral hygiene, as described in Example 6 below.

These compositions can also be used to treat bacterial infections of other body tissues, such as bacterial infections of the skin including, but not limited to, impetigo, folliculitis, acne and furuncolosis, and bacterial infections of mucous membranes such as vaginal tissue, anal tissue, oral cavity tissue, tissue of other orifices and ocular tissue. Fungal, viral and parasitic infections may also be treated.

In addition, conditions which are not the direct result of infection by an infectious agent, such as a bacterium, virus, fungus or parasite, can also be treated with the compositions of the present invention. Such conditions include the sites of insect bites, first-degree burns and areas of general inflammation, with or without the presence of an infectious agent.

The following is a general list of other diseases and conditions which can be treated with the compositions of the present invention. It is intended for illustrative purposes only and is not meant to be limiting. The diseases and conditions include: psoriasis, *Herpes zoster* infection, contact dermatitis, Condyloma catum, atopic eczema, seborrhea, Varicella infection, pemphigus, Varicola infection, Verruca, seborrheic dermatitis or keratosis, ulcers, *Herpes simplex* infection, glossitis, dental ulcers, stomatitis, aphthous ulcers, leukoplakia, abscesses, skin wounds and inflammation, primary and secondary skin infections including, but not limited to, varicose ulcers and contagiosa, diaper rash, skin irritation, eczema dermatos, itching, pruritis, urticaria, ichthyosis, hyperkeratotic skin, allergic dermatitis and infected eczema.

EXAMPLE 6

Mouthwash for Oral Hygiene

Hygiene of the oral cavity is important for dental care, as well as for overall good health. Oral hygiene has cosmetic implications as well, since poor oral hygiene can result in malodorous breath. One important aspect of oral hygiene is the inhibition of growth of bacteria which can cause caries and malodorous breath. Such inhibition of bacterial growth can be accomplished by rinsing of the oral cavity with a mouthwash solution.

As noted in the Background section above, simply finding anti-bacterial activity of a herbal preparation is not sufficient for its use as a medicine. Like all medicines, the herbal preparation must be used in a manner which is safe and effective. The safety of such a preparation is generally increased as the concentration of the active ingredient or ingredients is lowered, since the severity of side effects of medicines in the body is directly related to the concentration of the medicine present. However, as the concentration is lowered, the effectiveness of the medicine can also be reduced. Thus, a balance is required between these two goals.

The addition of a second ingredient, which is inactive alone but which shows synergistic activity in combination with the active ingredient, can help both goals to be obtained. Since a lower concentration of the active ingredient, essential oil, is required in the presence of the tincture, the combination is more likely to be safe. On the other hand, the combination is also more likely to be effective, given the synergistic anti-bacterial activity.

With these results in mind, the following mouthwash formulation of a combination of an essential oil and a tincture for oral hygiene were prepared. This formulation is intended as an illustrative example only and is not intended to be limiting in any way.

The following procedure was used to prepare the mouthwash. All percentages are given as percent weight per weight. The active ingredients in the mouthwash are an essential oil and a tincture which show synergistic anti-bacterial activity. Although other ingredients may show anti-bacterial activity, such activity is secondary to their other functions. Hence, these other ingredients are described as forming the pharmaceutical carrier for the two active, anti-bacterial ingredients.

The remaining ingredients preferably include alcohol, present in a concentration of from about 0% to about 25%, preferably from about 5% to about 15%. Alcohol contributes to the anti-bacterial activity of the mouthwash, as well as enhancing flavor and providing a refreshing sensation in the oral cavity. Another preferred ingredient is flavor, added to make the mouthwash more pleasant to use and to cosmetically enhance breath aroma. A third preferred ingredient is fluoride, which has anti-caries activity. A fourth preferred ingredient is a surfactant, which can solubilize flavors, aid removal of debris from the oral cavity and even provide anti-bacterial activity. Surfactants can be cationic, such as cetylpyridinium chloride; anionic, such as sodium lauryl sulfate, for example; Tween, Pluronic or any other food or pharmaceutical grade surfactant. A fifth preferred ingredient is a humectant, such as glycerin, sorbitol and hydrogenated starch hydrolyzates, which are often added to provide body or viscosity to the mouthwash, as well as a sweet taste. A sixth preferred ingredient is an astringent salt, which forms a thin protective film on the oral mucosa, reducing the permeability of the mucosal cells. Zinc chloride is an example of such an astringent salt, which is considered safe for topical application to the oral mucosa and is therefore often used in mouthwashes.

One example of a preferred formulation is given in Table 5 below. This formulation is intended for illustrative purposes only and is not intended to be limiting. In this example, the tincture includes the extracts of Plantago, Hypericum, Coneflower and Propolis and the essential oil is cinnamon oil.

TABLE 5

Formulation of a Mouthwash with Tincture and Cinnamon Oil

| Ingredient | Percent (weight per weight) |
|---|---|
| water | 75.47 |
| propylene glycol | 10 |
| ethyl alcohol | 7.5 |
| polysorbate 80 | 1.8 |
| Plantago extract | 1.5 |
| Hypericum extract | 1.5 |
| Coneflower extract | 1.0 |
| Propolis extract | 1.0 |
| Cinnamon oil | 0.2 |
| Saccharin sodium salt | 0.03 |

The preferred method of preparing the mouthwash of the above formulation was as follows. First, propylene glycol and ethanol are mixed to form a mixture. Next, polysorbate 80 was added to the mixture. Cinnamon oil was then added and the entire mixture was preferably mixed for about ten minutes.

One by one, each extract of the tincture was added in any order. Thus, Plantago extract, Hypericum extract, Coneflower extract and Propolis extract were combined with the mixture to form a combination. After each addition, the mixture was preferably mixed for about ten minutes.

Next, water and a 0.3% solution of saccharin sodium salt was preferably added to the combination with stirring to form the mouthwash.

EXAMPLE 7

Oral Gel

Another formulation for administration of the compositions of the present invention to the oral cavity is as an oral gel. The following formulation is intended as an example only and is not meant to be limiting in any way.

TABLE 6

Formulation of an Oral Gel

| Ingredient | Percent (Weight per Weight) |
|---|---|
| Water | 14.37 |
| PEG 75 | 20.0 |
| PEG 8 | 20.0 |

TABLE 6-continued

Formulation of an Oral Gel

| Ingredient | Percent (Weight per Weight) |
|---|---|
| Poloxamer 407 | 20.0 |
| Propylene Glycol | 8.0 |
| Polyacrylamide/C13-14 Isoparaffin/lauret-7 | 6.0 |
| Phytolaca Extract | 3.0 |
| Calendula Extract | 3.0 |
| Coneflower Extract | 2.0 |
| Propolis Extract | 2.0 |
| Tea-tree Oil | 0.6 |
| Ethyl alcohol | 0.5 |
| Tocopherol succinate | 0.3 |
| EDTA | 0.2 |
| Saccharin sodium salt | 0.03 |

EXAMPLE 8

Acne Cream

The synergistic compositions of the present invention can also be used to treat skin disorders such as acne. The following formulation, given in Table 7, is intended as an example only and is not intended to be limiting.

TABLE 7

Acne Cream

| Ingredient | Percent Weight per Weight |
|---|---|
| Water | 48.0 |
| Safflower Oil | 10.0 |
| Beeswax | 5.0 |
| Cetearyl octanoate | 5.0 |
| Cetearyl glucoside | 5.0 |
| Glycerol | 5.0 |
| Phytolacca Extract | 4.6 |
| Coneflower Extract | 4.6 |
| Symphytum Extract | 3.1 |
| Calendula Extract | 3.1 |
| Hamamelis Extract | 3.1 |
| Propolis Extract | 1.5 |
| Polyacrylamide/C13-14 Isoparaffin/lauret-7 | 1.0 |
| Thyme Oil | 0.5 |
| Lavandula Oil | 0.5 |

EXAMPLE 9

Impetigo Cream

A second example of a formulation with a synergistic composition of the present invention for the treatment of skin disorders such as impetigo and related infections is given below. The following formulation, given in Table 8, is intended as an example only and is not intended to be limiting.

TABLE 8

Impetigo Cream

| Ingredient | Percent Weight per Weight |
|---|---|
| Water | 54.0 |
| Caprylic/Capric triglyceride | 10.0 |
| Beeswax | 5.0 |
| Cetearyl octanoate | 5.0 |

TABLE 8-continued

Impetigo Cream

| Ingredient | Percent Weight per Weight |
| --- | --- |
| Cetearyl glucoside | 5.0 |
| Glycerine | 5.0 |
| Burdock Extract | 4.0 |
| Coneflower Extract | 3.0 |
| Baptisia Extract | 2.0 |
| Myrrh Extract | 2.0 |
| Propolis Extract | 2.0 |
| Polyacrylamide/C13-14 Isoparaffin/lauret-7 | 1.0 |
| Thyme Oil | 1.0 |
| Sweet Marjoram Oil | 1.0 |

EXAMPLE 10

Skin Gel

Another example of a formulation with a synergistic composition of the present invention for the treatment of skin disorders such as contact dermatitis and eczema is in the form of a skin gel. The following formulation, given in Table 9, is intended as an example only and is not intended to be limiting.

TABLE 9

Skin Gel

| Ingredient | Percent Weight per Weight |
| --- | --- |
| Water | 68.75 |
| PEG 8 | 7.0 |
| Chickweed Extract | 2.0 |
| Cetearyl octanoate | 6.0 |
| Calendula Extract | 2.0 |
| Witch Hazel Extract | 2.0 |
| Burdock Extract | 3.0 |
| Comfrey Extract | 2.0 |
| Baptisia Extract | 2.0 |
| Ethyl Alcohol | 0.75 |
| Tocopheryl Succinate | 0.5 |
| Polyacrylamide/C13-14 Isoparaffin/lauret-7 | 4.0 |
| Thyme Oil | 0.5 |
| Sweet Marjoram Oil | 0.5 |

While the invention has been described with respect to a limited number of embodiments, it will be appreciated that many variations, modifications and other applications of the invention may be made.

What is claimed is:

1. A synergistic anti-microbial composition, comprising a herbal extract and an essential oil in a synergistic ratio, wherein said essential oil is cinnamon oil, said cinnamon oil being present in a concentration in a range of from about 0.01 percent to about 0.5 percent weight per weight and wherein said herbal extract is a mixture of Plantago, Hypericum, Echinacea and Propolis, said Plantago and said Hypericum being present in a concentration in a range of from about 0.1 percent to about 2 percent weight per weight, and said Echinacea and said Propolis being present in a concentration in a range of from about 0.1 percent to about 1.0 percent weight per weight.

2. The composition of claim 1, wherein said herbal extract is a tincture.

3. The composition of claim 1, further comprising a suitable pharmaceutical carrier.

4. A method of treating a subject with a microbial infection, comprising the step of administering a synergistic anti-microbial composition to the subject, said composition including a herbal extract and an essential oil in a synergistic ratio, wherein said essential oil is cinnamon oil, said cinnamon oil being present in a concentration in a range of from about 0.01 percent to about 0.5 percent weight per weight and wherein said herbal extract is a mixture of Plantago, Hypericum, Echinacea and Propolis, said Plantago and said Hypericum being present in a concentration in a range of from about 0.1 percent to about 2 percent weight per weight, and said Echinacea and said Propolis being present in a concentration in a range of from about 0.1 percent to about 1.0 percent weight per weight.

5. The method of claim 4, wherein said microbial infection is selected from the group consisting of bacterium, fungus, virus and parasite.

6. The composition of claim 1, wherein the composition is a mouthwash.

7. The composition of claim 1, wherein said cinnamon oil is present in a concentration in a range of from about 0.03 percent to about 0.15 percent weight per weight.

8. The composition of claim 1, wherein said Plantago and said Hypericum are present in a concentration in a range of from about 0.5 percent to about 1.3 percent weight per weight, and said Echinacea and said Propolis are present in a concentration in a range of from about 0.3 percent to about 0.8 percent weight per weight.

9. The composition of claim 1, wherein a ratio of said Plantago to said Hypericum to said Echinacea to said Propolis is about 3:3:2:2.

10. The method of claim 4, wherein said cinnamon oil is present in a concentration in a range of from about 0.03 percent to about 0.15 percent weight per weight.

11. The method of claim 4, wherein said Plantago and said Hypericum are present in a concentration in a range of from about 0.5 percent to about 1.3 percent weight per weight, and said Echinacea and said Propolis are present in a concentration in a range of from about 0.3 percent to about 0.8 percent weight per weight.

12. The method of claim 4, wherein a ratio of said Plantago to said Hypericum to said Echinacea to said Propolis is about 3:3:2:2.

* * * * *